(12) United States Patent
Shin et al.

(10) Patent No.: US 7,365,228 B2
(45) Date of Patent: *Apr. 29, 2008

(54) METHOD FOR PRODUCING UNSATURATED FATTY ACIDS

(75) Inventors: Hyun Jong Shin, Gwangju (KR); Byung Yul Choi, Naju-si (KR); Young Jin Cho, Naju-si (KR); Yeon Shick Yoo, Naju-si (KR); Young Hyun Choi, Jeollanam-do (KR); Duk Ki Kim, Gwangju (KR); Joo Yeon Park, Gwangju (KR)

(73) Assignee: LG Chem, Ltd. (KR)

( * ) Notice: Subject to any disclaimer, the term of this patent is extended or adjusted under 35 U.S.C. 154(b) by 15 days.

This patent is subject to a terminal disclaimer.

(21) Appl. No.: 11/344,716

(22) Filed: Feb. 1, 2006

(65) Prior Publication Data

US 2006/0211883 A1    Sep. 21, 2006

(30) Foreign Application Priority Data

Feb. 1, 2005  (KR) ..................... 10-2005-0009128

(51) Int. Cl.
*C07C 51/16* (2006.01)
(52) U.S. Cl. .................................... 562/547
(58) Field of Classification Search ............. None
See application file for complete search history.

(56) References Cited

U.S. PATENT DOCUMENTS

| 4,256,783 | A | * | 3/1981 | Takada et al. | ............... 422/197 |
| 5,198,581 | A | * | 3/1993 | Kawajiri et al. | ............ 562/546 |
| 6,028,220 | A | | 2/2000 | Wada et al. | |
| 6,399,818 | B2 | | 6/2002 | Tanimoto et al. | |
| 6,563,000 | B1 | | 5/2003 | Yunoki et al. | |
| 6,657,080 | B2 | | 12/2003 | Yunoki et al. | |
| 7,151,184 | B2 | * | 12/2006 | Storck et al. | ............... 549/240 |

FOREIGN PATENT DOCUMENTS

| DE | 2513405 | | 10/1976 |
| EP | 0383224 A2 | | 8/1990 |
| EP | 0911313 A1 | | 4/1999 |
| JP | 53-030688 | * | 3/1978 |
| JP | 07-010802 | * | 1/1995 |
| JP | 09241209 | | 9/1997 |
| JP | 11-080052 | * | 3/1999 |
| JP | 11086286 | | 3/1999 |
| JP | 2000-336060 | | 12/2000 |
| JP | 2001-129384 | * | 5/2001 |
| JP | 2001-137689 | * | 5/2001 |
| JP | 2001-139499 | * | 5/2001 |
| JP | 2001129384 | | 5/2001 |
| JP | 2001-354612 | | 12/2001 |
| KR | 1020010080871 A | * | 8/2001 |
| WO | 03/070680 A1 | | 8/2003 |
| WO | WO 03/070680 A1 | * | 8/2003 |

OTHER PUBLICATIONS

International Search Report for International Application No. PCT/KR2006/000343; Filing Date Feb. 1, 2006, Date of Mailing Apr. 24, 2006.

* cited by examiner

*Primary Examiner*—Sikarl A. Witherspoon
(74) *Attorney, Agent, or Firm*—Cantor Colburn LLP

(57) ABSTRACT

Disclosed is a method for producing unsaturated fatty acids from unsaturated aldehydes by means of fixed-bed catalytic partial oxidation in a shell-and-tube reactor, characterized in that the reactor includes a reaction zone for producing unsaturated fatty acids, the reaction zone having an inactive material layer inserted into a position where a hot spot is to be generated in a reaction tube. A fixed-bed shell-and-tube reactor for use in the above method is also disclosed. According to the present invention, at least one layer of inactive material is packed at the point of a hot spot to control the hot spot temperature efficiently, thereby increasing the lifetime of a catalyst and producing unsaturated fatty acids with high yield.

9 Claims, 2 Drawing Sheets

METHOD FOR PRODUCING UNSATURATED FATTY ACIDS

This application claims the benefit of the filing date of Korean Patent Application No. 2005-9128, filed on Feb. 1, 2005, in the Korean Intellectual Property Office, the disclosure of which is incorporated herein in its entirety by reference.

TECHNICAL FIELD

The present invention relates to a method for producing unsaturated acids from unsaturated aldehydes by means of fixed-bed catalytic partial oxidation in a shell-and-tube heat exchange type reactor, as well as to a fixed-bed shell-and-tube heat exchange type reactor used in the above method.

BACKGROUND ART

A process for producing unsaturated aldehydes and then unsaturated acids from olefins is a typical example of catalytic vapor phase oxidation.

To perform the partial oxidation of olefins, a multimetal oxide containing molybdenum and bismuth or vanadium or a mixture thereof is used as a catalyst. Typically, the partial oxidation of olefins may be exemplified by a process for producing (meth)acrolein and then (meth)acrylic acid by oxidizing propylene or isobutylene, a process for producing phthalic anhydride by oxidizing naphthalene or ortho-xylene or a process for producing maleic anhydride by partially oxidizing benzene, butylene or butadiene.

Generally, propylene or isobutylene is subjected to two-step catalytic vapor phase partial oxidation to form (meth)acrylic acid as a final product. More particularly, in the first step, propylene or isobutylene is oxidized by oxygen, diluted inert gas, water vapor and an optional amount of catalyst to form (meth)acrolein as a main product. In the second step, (meth)acrolein obtained from the preceding step is oxidized by oxygen, diluted inert gas, water vapor and an optional amount of catalyst to form (meth)acrylic acid. The catalyst used in the first step is a catalyst comprising an oxide and/or a composite oxide based on Mo—Bi, which oxidizes propylene or isobutylene to form (meth)acrolein as a main product. Additionally, a part of (meth)acrolein is further oxidized on the same catalyst to form (meth)acrylic acid partially. The catalyst used in the second step is a catalyst comprising an oxide and/or a composite oxide based on Mo—V, which oxidizes (meth)acrolein-containing mixed gas produced in the first step, particularly (meth)acrolein, to form (meth)acrylic acid as a main product.

Reactors for carrying out the above process are realized in such a manner that each of the above two steps are implemented in one system or in two different systems (see U.S. Pat. No. 4,256,783).

Generally, (meth)acrylic acid is reacted with alcohol, to form (meth)acrylate, which is used for paints, fiber formula, coating agent of paper. Especially, a high purity of acrylic acid is used as a raw material for a highly hygroscopic resin, and a demand thereof is recently increasing rapidly.

In general, catalytic vapor phase oxidation is implemented as follows. At least one catalyst in the form of granules is packed into reaction tubes, feed gas is supplied to a reactor through the reaction tubes and the feed gas is in contact with the catalyst in the reaction tubes to perform vapor phase oxidation. Reaction heat generated during the reaction is removed by heat transfer with a heat transfer medium, wherein the temperature of the heat transfer medium is maintained at a predetermined temperature. Particularly, the heat transfer medium for heat exchange is provided on the outer surface of the catalytic tubes to perform heat transfer. A reaction product mixture containing a desired product is collected via a duct and then sent to a purification step. Generally, catalytic vapor phase oxidation is a highly exothermic reaction. Therefore, it is very important to control the reaction temperature in a specific range and to downsize hot spots in the reaction zone.

Vapor phase partial oxidation for producing unsaturated acids from unsaturated aldehydes is an exothermic reaction. Therefore, it has a problem in that a hot spot (a point whose temperature is abnormally high) is generated in the reactor. Such hot spots show a relatively high temperature compared to other parts of the reactor. Accordingly, in hot spots, complete oxidation proceeds rather than partial oxidation, thereby increasing by-products such as COx and decreasing the yield of unsaturated acids. Additionally, excessive heat generated in a hot spot causes migration or sublimation of molybdenum that is a main element of the catalyst, resulting in deposition of molybdenum in a catalytic layer and pressure drop in the catalytic layer, degradation of catalytic activity and in shortening of the lifetime of the catalyst. Therefore, yield of unsaturated acid decreases.

Generally, various methods are known in order to control the excessive heat at a hot spot in a catalytic reaction accompanied with heat generation. Such methods include a method for reducing the amount of feed gas to decrease the space velocity and a method of using a reaction tube having a relatively small inner diameter. However, when the space velocity decreases, it is not possible to obtain high productivity in an industrial scale. When the inner diameter of a reaction tube decreases, it is difficult to manufacture the reactor. Moreover, in the latter case, there are disadvantages of economically unfavorable high cost needed for manufacturing the reactor, and increased time and labor needed for packing a catalyst. For these reasons, there has been a continuous need for and research into a method for producing unsaturated aldehydes and/or unsaturated fatty acids with high yield and high productivity by using a catalyst stably for a long time, while avoiding the above problems according to the known methods.

For example, Such methods include a method for packing a catalytic bed by controlling the volume of catalyst in such a manner that the volume gradually decreases from the inlet to the outlet(Japanese Laid-Open Patent No. Hei9-241209); a method for packing a catalytic bed by controlling the volume of catalyst particle in such a manner that the volume gradually decreases from the inlet to the outlet; a method for preparing acrylic acid by multistage-packing with catalysts having different activities; a method of dividing inside of a reaction tube into a plurality of reaction zones and packing each catalyst therein; a method for packing a catalytic bed by controlling the activity of catalyst in such a manner that the activity gradually increases from the inlet to the outlet (Japanese Laid-Open Patent No. 2000-336060); a method for packing a catalytic bed by controlling the amount of catalyst supported on carrier in such a manner that the activity gradually increases from the inlet to the outlet(US No. 2000-336060); a method for packing a catalytic bed wherein a first reaction zone most adjacent to the inlet is packed with the catalyst having higher activity than that of the second reaction zone adjacent thereto and then the catalytic bed from second reaction zone is packed by controlling the activity of catalyst in such a manner that the activity gradually increases from the inlet to the outlet (Japanese Laid-Open Patent No. 2001-112617). However, the above mentioned methods for minimizing degradation of catalyst and suppressing side reactions by decreasing the temperatures of hot spots are not fully effective to solve the above described problems.

Therefore, there is a continuous need for a method for minimizing degradation of catalyst and side reactions caused by extreme heat generation at a hot spot generated during the catalytic reaction.

DISCLOSURE OF THE INVENTION

Figure 1:
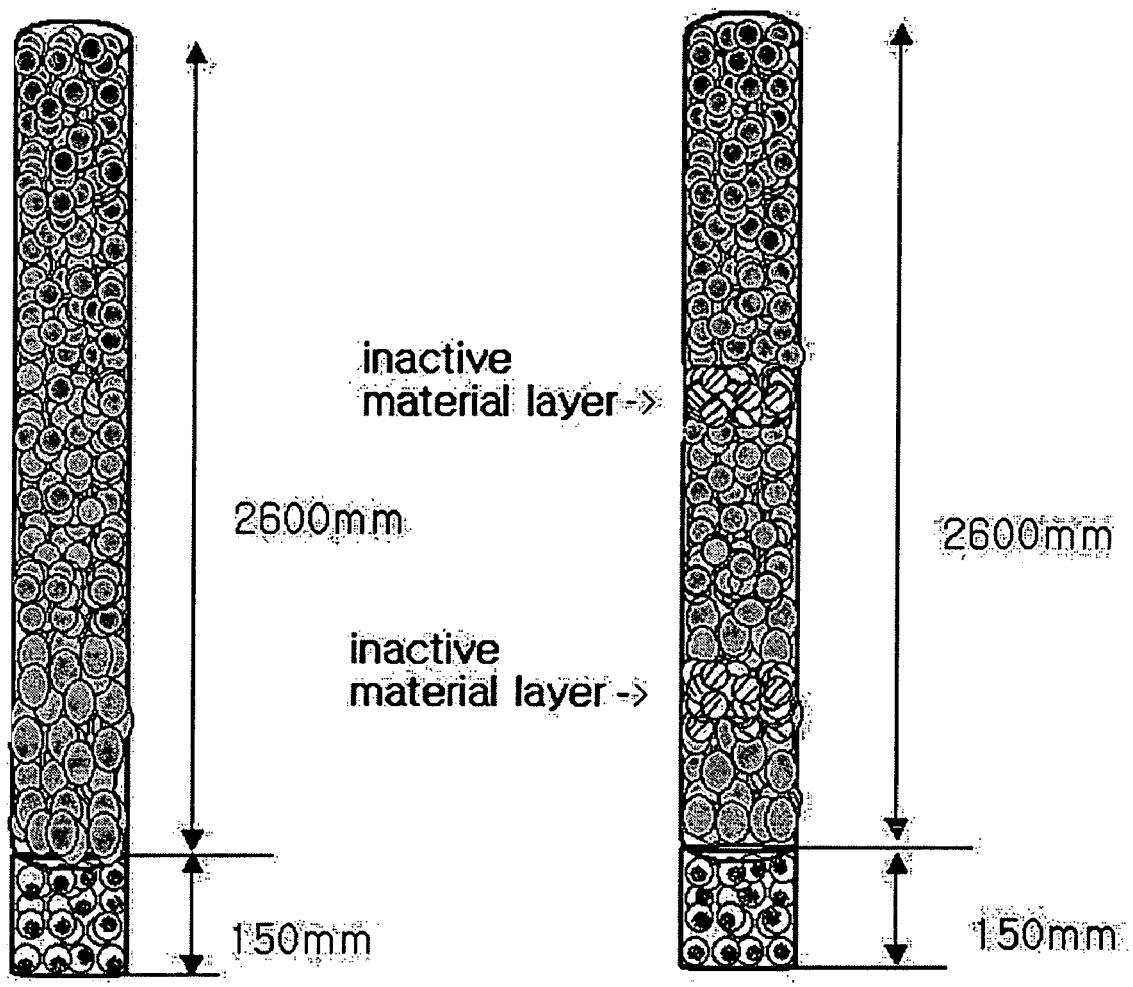
FIG. 1 is a schematic view showing the structure of a reactor according to Comparative Example 2 and Example 2, including catalytic layers and an inactive material layer packed therein.

It is an object of the present invention to minimize sublimation and/or migration of molybdenum that is a main element of the catalyst, pressure-drop in catalytic layer and degradation of catalytic activity, all of which occur at a hot spot, and to increase the lifetime of catalyst. In order to achieve the object, the present invention provides a method for producing unsaturated fatty acids with high yield in a stable manner for a long time, the method including estimating the position of a hot spot in a reaction tube and packing an inactive material layer into the hot spot to reduce heat generation at the hot spot, thereby facilitating heat control and/or to disperse a temperature distribution toward a reaction gas outlet.

According to an aspect of the present invention, there is provided a method for producing unsaturated fatty acids (ex. (meth)acrylic acid) from unsaturated aldehydes (ex. (meth) acrolein) by means of fixed-bed catalytic partial oxidation in a shell-and-tube reactor, characterized in that the reactor includes a reaction zone for producing unsaturated acids, the reaction zone having an inactive material layer inserted into a position where a hot spot is to be generated in a reaction tube.

According to another aspect of the present invention, there is provided a shell-and-tube reactor that may be used in a method for producing unsaturated fatty acids from unsaturated acids by means of fixed-bed catalytic partial oxidation, characterized in that the reactor includes a reaction zone for producing unsaturated acids, the reaction zone having an inactive material layer inserted into a position where a hot spot is to be generated in a reaction tube.

Hereinafter, the present invention will be explained in detail.

According to the present invention, an inactive material layer is formed at the position of a hot spot in the reactor so that partial oxidation at the hot spot can be prevented, thereby minimizing heat generation at the hot spot and dispersing the temperature distribution, resulting in minimization of degradation of catalyst and side reactions.

As used herein, the term "hot spot" is referred to as a point where a peak temperature is generated. For example, a hot spot may be a point where an abnormally high temperature is maintained due to excessive heat generation or heat accumulation, in a catalytic bed in the reaction tube of the reaction zone for producing unsaturated acids from unsaturated aldehydes.

A hot spot is formed by the reaction heat generated during catalytic vapor phase oxidation. The position and size of a hot spot are determined by many factors including a reactant composition, space velocity and temperature of heat transfer medium. Under constant processing conditions, a hot spot has a constant position and size. Therefore, the position of a hot spot can be estimated by using a simulation method, etc.

In general, each catalytic layer has at least one hot spot. The hot spot may be generated at the front part of the catalytic bed for the oxidation, enriched with a main reactant (unsaturated aldehydes) and molecular oxygen. In addition, the hot spot may be generated at the vicinity of the border of adjacent catalytic layers having different activities, in the case of a reactor structure packed with two or more catalytic layers.

Figure 2:
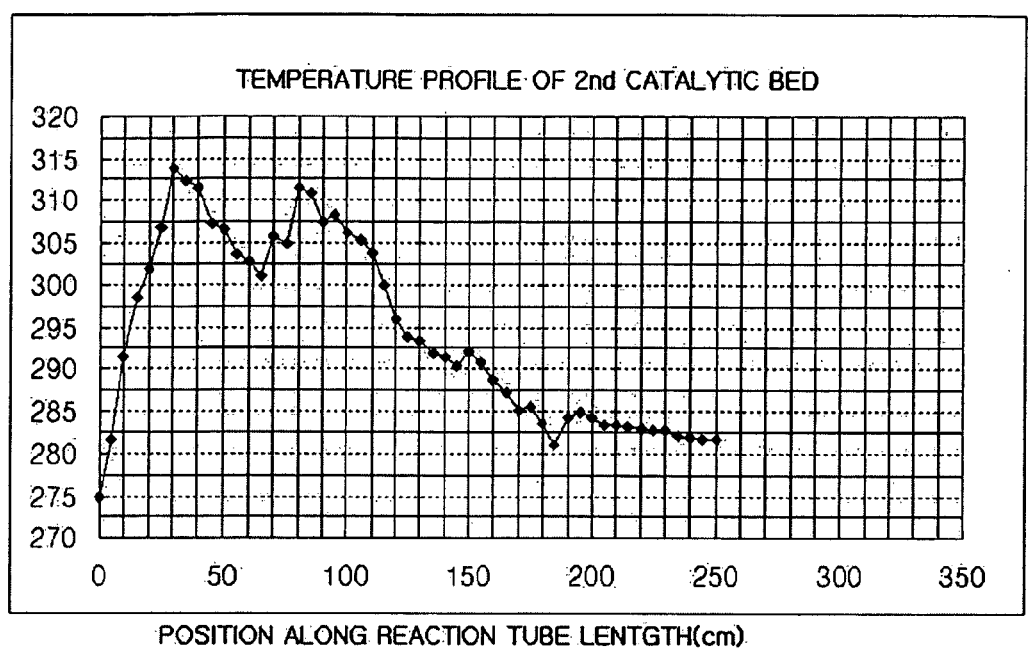
FIG. 2 is a graph showing the temperature profile of a catalyst bed at 270° C. in a reaction zone for producing unsaturated acids from unsaturated aldehydes.

According to the present invention, the position of a hot spot and the temperature peak size of a hot spot are quantitatively analyzed based on the temperature profile (see FIG. 2) of a catalytic bed in a reaction tube. Then, a predetermined height of an inactive material layer is inserted into the temperature peak position where a hot spot is generated so as to prevent partial oxidation at the hot spot, thereby minimizing heat generation at the hot spot and dispersing a temperature distribution.

The reactors that may be used in the present invention include a fixed-bed multi-tube reactor and a conical fixed-bed multi-tube reactor. There is no particular limitation on the shape of the reactor. In order to form a catalytic bed needed for carrying out vapor phase partial oxidation, a catalyst is packed in the reaction tube of a reactor, an inactive material is packed at the position of a hot spot, in one layer or two or more layers having different kinds and sizes of inactive material, and then the catalyst is further packed in the reaction tube.

In the case of the reaction zone for producing unsaturated acids from unsaturated aldehydes, a catalytic bed may be packed in one layer having uniform activity along the axial direction, or in two or more layers whose catalytic activity gradually increases along the axial direction, if necessary.

Preferably, the catalyst used in the vapor phase partial oxidation for producing unsaturated fatty acids is a metal oxide represented by the following formula 1:

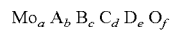
$$Mo_a A_b B_c C_d D_e O_f \qquad \text{[formula 1]}$$

wherein Mo is molybdenum;

A is at least one element selected from the group consisting of W and Cr;

B is at least one element selected from the group consisting of P, Te, As, B, Sb, Ce, Pb, Mn, V, Nb, and Te;

C is at least one element selected from the group consisting of Si, Al, Zr, Rh, Cu, Ni, Ti, Ag and Sn;

D is at least one element selected from the group consisting of Na, K, Li, Rb, Cs, Ta, Ca, Mg, Sr, Ba and MgO; and each of a, b, c, d, e and f represents the atomic ratio of each element, with the proviso that when a=12, b is a number of between 0.01 and 10, c is a number of between 0.01 and 10, d is a number of between 0.01 and 10, e is a number of between 0.01 and 10, and f is a number defined depending on the oxidation state of each of the above elements.

The catalyst may be supported on carrier having a cylindrical, a hollow cylindrical or spheral shape, and there is no particular limitation in shape of the carrier. The catalyst having a cylindrical shape preferably has an aspect ratio (the ratio of length to diameter (outer diameter), i.e., L/D) of between 1 and 1.3. More preferably, the ratio of L/D equals 1. The catalyst having a cylindrical or spherical shape has an outer diameter of preferably 3~10 mm, and more preferably 5~8 mm.

The inactive material layer that may be used in the present invention may be formed of an inactive material alone or a mixture of an inactive material with a catalyst. However, when a mixture of an inactive material with a catalyst is used, the activity of the mixture should be lower than that of a catalytic layer in the vicinity of a hot spot. The volume ratio of the inactive material to the catalyst in the inactive material layer is preferably 20-100%, and more preferably 80-100%.

The inactive material that may be used in the present invention is referred to as material inactive to a reaction for producing unsaturated acids from unsaturated aldehydes such as catalytic oxidation of (meth)acrolein. Such inactive materials include silica, alumina, silica/alumina, zirconium oxide, titanium oxide, mixtures thereof, etc.

Although there is no particular limitation in shape of the inactive material, the inactive material may have the shape of a sphere, cylinder, ring, rod, and mass with a suitable size. If necessary, mixtures of the above shapes may be used.

When the inactive material has the shape of a sphere, cylinder and ring, the diameter is preferably 2-10 mm, and more preferably 5-8 mm. When the inactive material has the shape of a cylinder and ring, the ratio of length to diameter (L/D) is preferably 1-1.3, and more preferably is 1. Preferably, the inactive material has the same or similar shape and/or size as the catalyst.

At the point of a hot spot, the inactive material layer is packed to the height of 0.1-1000 mm, preferably to the height of 10-200 mm, in one or more layers, preferably in one or two layers. The position where the inactive material layer is disposed in a reaction tube ranges preferably 1-80% and more preferably 1-60% of the total length of the whole catalytic bed in the reaction zone producing unsaturated acid, when viewed from the reaction gas inlet toward the outlet.

It is preferable that the temperature at the hot spot of a reactor is controlled by the inactive material layer inserted into the hot spot, in such a manner that the temperature of the hot spot is equal to or lower than (reaction temperature+ 45° C.). Accordingly, it is possible to minimize sublimation of catalytically active components and to inhibit side reactions caused by excessive heat, thereby increasing the lifetime of a catalyst and producing unsaturated fatty acids from unsaturated aldehydes with high yield.

Vapor phase partial oxidation for producing unsaturated acids in a reactor having an inactive layer at the hot spot according to the present invention is suitably carried out at a reaction temperature of 200-450° C., preferably 265-370° C., under a reaction pressure of 0.1-10 atm, preferably 0.5-3 atm. For example, in order to perform oxidation, a feed gas including 5-10 volume % of a feed compound such as (meth)acrolein, 10-13 volume % of oxygen, 5-60 volume % of water vapor and 20-80 volume % of an inert gas is introduced onto a catalyst at a space velocity of 500-5000 $hr^{-1}$ (STP)

MODE FOR CARRYING OUT THE INVENTION

Reference will now be made in detail to the preferred embodiments of the present invention. It is to be understood that the following examples are illustrative only and the present invention is not limited thereto.

PREPARATION EXAMPLE 1

(Preparation of Catalyst)

2000 ml of distilled water was heated with stirring at 100° C. and 246 g of ammonium tungstate, 1000 g of ammonium molybdate and 220 g of ammonium vanadate were dissolved therein to form solution (1). To 500 ml of distilled water, 228 g of copper nitrate, 49 g of strontium nitrate and 25 g of niobium hydroxide were added and mixed thoroughly to form solution (2). Solution (1) was mixed with solution (2), to from a catalyst suspension.

The suspension obtained as described above was treated by a homogenizer for 30 minutes or more, and then 20-30 wt % of catalytically active components (to the total weight of the supported catalyst) in the suspension state were coated on each spheral carrier having outer diameter of 4.0-8.0 mm using a spray nozzle. The resultant was dried at 120° C. and baked at 400° C. for 5 hours to form spherical catalysts having outer diameters of 4.5 mm(±0.2), 5 mm(±0.2), 8 mm(±0.2), respectively.

Herein, the resultant catalytically active component except oxygen had the composition of: $Mo_{12}$, $W_{2.0}$, $Nb_{0.2}$, $V_{4.0}$, $Cu_{2.0}$, $Sr_{0.5}$

COMPARATIVE EXAMPLE 1

To a stainless steel reactor having an inner diameter of 1 inch and heated with molten nitrate, alumina/silica as an inactive material was packed to the height of 150 mm, and then the catalyst obtained from Preparation Example 1 and having a size of 5 mm(±0.2) was packed to the height of 2600 mm, when viewed from the reaction gas inlet toward the outlet.

EXAMPLE 1

To a stainless steel reactor having an inner diameter of 1 inch and heated with molten nitrate, alumina/silica as an inactive material was packed to the height of 150 mm, the catalyst obtained from Preparation Example 1 and having a size of 5 mm(±0.2) was packed to the height of 300 mm, alumina/silica as an inactive material was packed to the height of 100 mm at the point of a hot spot, and then the catalyst obtained from Preparation Example 1 and having a size of 5 mm(±0.2) was further packed to the height of 2200 mm, when viewed from the reaction gas inlet toward the outlet.

COMPARATIVE EXAMPLE 2

To a stainless steel reactor having an inner diameter of 1 inch and heated with molten nitrate, alumina/silica as an inactive material was packed to the height of 150 mm, the catalyst obtained from Preparation Example 1 and having a size of 8 mm(±0.2) was packed to the height of 800 mm, and then the catalyst obtained from Preparation Example 1 and having a size of 5 mm(±0.2) was further packed to the height of 2000 mm, when viewed from the reaction gas inlet toward the outlet.

EXAMPLE 2

To a stainless steel reactor having an inner diameter of 1 inch and heated with molten nitrate, alumina/silica as an inactive material was packed to the height of 150 mm, the catalyst obtained from Preparation Example 1 and having a size of 8 mm(±0.2) was packed to the height of 300 mm, alumina/silica as an inactive material was packed to the height of 100 mm at the point of a hot spot, and then the catalyst obtained from Preparation Example 1 and having a size of 8 mm(±0.2) was further packed to the height of 200 mm, when viewed from the reaction gas inlet toward the outlet. Further, the catalyst obtained from Preparation Example 1 and having a size of 5 mm(±0.2) was packed to the height of 100 mm, alumina/silica as an inactive material was packed to the height of 100 mm at the point of a hot spot, and then the catalyst obtained from Preparation Example 1 and having a size of 5 mm(±0.2) was packed to the height of 1800 mm.

COMPARATIVE EXAMPLE 3

To a stainless steel reactor having an inner diameter of 1 inch and heated with molten nitrate, alumina/silica as an inactive material was packed to the height of 150 mm, the catalyst obtained from Preparation Example 1 and having a size of 8 mm(±0.2) was packed to the height of 600 mm, the catalyst obtained from Preparation Example 1 and having a size of 4.5 mm(±0.2) was packed to the height of 1000 mm, and then the catalyst obtained from Preparation Example 1 and having a size of 5 mm(±0.2) was packed to the height of 1000 mm, when viewed from the reaction gas inlet toward the outlet.

EXAMPLE 3

To a stainless steel reactor having an inner diameter of 1 inch and heated with molten nitrate, alumina/silica as an inactive material was packed to the height of 150 mm, the catalyst obtained from Preparation Example 1 and having a size of 8 mm(±0.2) was packed to the height of 300 mm, alumina/silica as an inactive material was packed to the height of 100 mm at the point of a hot spot, and then the catalyst obtained from Preparation Example 1 and having a size of 8 mm(±0.2) was further packed to the height of 200 mm, when viewed from the reaction gas inlet toward the outlet. Next, the catalyst obtained from Preparation Example 1 and having a size of 4.5 mm(±0.2) was packed to the height of 100 mm, alumina/silica as an inactive material was packed to the height of 100 mm at the point of a hot spot, and then the catalyst obtained from Preparation Example 1 and having a size of 4.5 mm(±0.2) was packed to the height of 800 mm. Further, alumina/silica as an inactive material was packed to the height of 100 mm at the point of a hot spot, and then the catalyst obtained from Preparation Example 1 and having a size of 5 mm(±0.2) was packed to the height of 900 mm.

COMPARATIVE EXAMPLE 4

The same catalyst, inactive material and packing heights as Comparative Example 3 were used to provide a reactor, except that a stainless steel fixed-bed conical multi-tube reactor was used instead of the stainless steel reactor having an inner diameter of 1 inch.

EXAMPLE 4

The same catalyst, inactive material and packing heights as Example 3 were used to provide a reactor, except that a stainless steel fixed-bed conical multi-tube reactor was used instead of the stainless steel reactor having an inner diameter of 1 inch.

EXPERIMENTAL EXAMPLE

Catalytic Activity Test

The reactors packed with catalysts according to the above Examples and Comparative Examples were used to perform oxidation of acrolein, thereby producing acrylic acid. The oxidation was carried out by introducing a feed gas containing 7 volume % of acrolein, 5.6 volume % of oxygen, 15 volume % of water vapor and 72.4 volume % of inert nitrogen onto the catalyst at the reaction temperature of 265-300° C., under the reaction pressure of 1-3 atm, at the space velocity of 500-2000 $hr^{-1}$ (STP).

The results obtained from the above Examples and Comparative Examples are shown in the following Table 1.

In Table 1, the reactant (acrolein) conversion ratio, selectivity and yield are calculated based on the following mathematical formulae 1 and 2.

acrolein conversion ratio (%)=[moles of reacted acrolein/moles of supplied acrolein]×100 [mathematical formula 1]

yield (%) of acrylic acid=[moles of produced acrylic acid/moles of supplied acrolein]×100 [mathematical formula 2]

TABLE 1

| Examples | Acrolein Conversion (%) (Reaction temp. of 276° C.) | Highest Hot Spot Temperature (° C.) | Yield of Acrylic Acid(%) |
| --- | --- | --- | --- |
| Comp. Ex. 1 | 97.76 | 340 | 85.33 |
| Ex. 1 | 99.43 | 320 | 86.56 |
| Comp. Ex. 2 | 98.72 | 326 | 85.12 |
| Ex. 2 | 99.37 | 319 | 87.76 |
| Comp. Ex. 3 | 97.13 | 328 | 85.26 |
| Ex. 3 | 98.67 | 316 | 86.84 |
| Comp. Ex. 4 | 99.40 | 327 | 86.85 |
| Ex. 4 | 99.43 | 318 | 87.32 |

As can be seen from Table 1, reactors of Examples 1-4 including at least one layer of inactive material formed at the point of a hot spot in the catalytic reaction zone according to the present invention can provide excellent acrolein conversion ratio and yield of a desired product of acrylic acid as well as a lower temperature in the point of heat generation.

INDUSTRIAL APPLICABILITY

As can be seen from the foregoing, the present invention provides a method for producing unsaturated fatty acids from unsaturated aldehydes such as (meth)acrolein, by means of fixed-bed catalytic vapor phase partial oxidation with molecular oxygen or molecular oxygen-containing gas in a shell-and-tube heat exchange type reactor. According to the present invention, it is possible to minimize the heat generation in hot spots, to disperse a temperature distribution toward an outlet, and thus to produce unsaturated fatty acids stably with high yield for a long time, by virtue of at least one layer of inactive material inserted into a position where a hot spot is to be generated in a reaction tube.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. A method for producing unsaturated fatty acids from unsaturated aldehydes by means of fixed-bed catalytic partial oxidation in a shell-and-tube reactor, characterized in that the reactor includes a reaction zone for producing unsaturated fatty acids, the reaction zone having an inactive material layer inserted into a position where a hot spot is to be generated in a reaction tube.

2. The method according to claim 1, wherein the catalyst for producing unsaturated fatty acids from unsaturated aldehydes is a metal oxide catalyst represented by the following formula 1:

$$Mo_a A_b B_c C_d D_e O_f \qquad \text{[formula 1]}$$

wherein Mo is molybdenum;
A is at least one element selected from the group consisting of W and Cr;
B is at least one element selected from the group consisting of P, Te, As, B, Sb, Ce, Pb, Mn, V, Nb, and Te;
C is at least one element selected from the group consisting of Si, Al, Zr, Rh, Cu, Ni, Ti, Ag and Sn;
D is at least one element selected from the group consisting of Na, K, Li, Rb, Cs, Ta, Ca, Mg, Sr, Ba and MgO; and
each of a, b, c, d, e and f represents the atomic ratio of each element, with the proviso that when a=12, b is a number of between 0.01 and 10, c is a number of between 0.01 and 10, d is a number of between 0.01 and 10, e is a number of between 0.01 and 10, and f is a number defined depending on the oxidation state of each of the above elements.

3. The method according to claim 1, which is for producing (meth)acrylic acid from (meth)acrolein.

4. The method according to claim 1, wherein the inactive material layer is formed of an inactive material alone or a mixture of an inactive material with a catalyst.

5. The method according to claim 4, wherein the inactive material is present in the inactive material layer in a ratio of between 20% and 100% based on the volume of the catalyst.

6. The method according to claim 1, wherein the inactive material layer is packed to a height of between 0.1 mm and 1000 mm.

7. The method according to claim 4, wherein the inactive material takes a spherical, cylindrical or ring shape and has a diameter of between 2 mm and 10 mm.

8. The method according to claim 1, wherein the temperature of the hot spot is controlled in such a manner that it is equal to or lower than reaction temperature+45° C.

9. The method according to claim 1, wherein the inactive material has the same size, shape or size and shape as the catalyst.

* * * * *